US012182529B2

United States Patent
Sehanobish et al.

(10) Patent No.: US 12,182,529 B2
(45) Date of Patent: Dec. 31, 2024

(54) MULTI-TASK ADAPTERS AND TASK SIMILARITY FOR EFFICIENT EXTRACTION OF PATHOLOGIES FROM MEDICAL REPORTS

(71) Applicant: Covera Health, New York, NY (US)

(72) Inventors: Arijit Sehanobish, Washington, DC (US); Anasuya Das, Teaneck, NJ (US); Benjamin Odry, West New York, NY (US)

(73) Assignee: Covera Health, New York, NY (US)

( * ) Notice: Subject to any disclaimer, the term of this patent is extended or adjusted under 35 U.S.C. 154(b) by 281 days.

(21) Appl. No.: 17/992,212

(22) Filed: Nov. 22, 2022

(65) Prior Publication Data

US 2023/0161978 A1 May 25, 2023

Related U.S. Application Data

(60) Provisional application No. 63/283,006, filed on Nov. 24, 2021.

(51) Int. Cl.
*G06F 40/00* (2020.01)
*G06F 40/295* (2020.01)
(Continued)

(52) U.S. Cl.
CPC ............ *G06F 40/58* (2020.01); *G06F 40/295* (2020.01); *G16H 10/60* (2018.01)

(58) Field of Classification Search
None
See application file for complete search history.

(56) References Cited

U.S. PATENT DOCUMENTS 10,499,857 B1    12/2019   Nguyen et al.
2019/0164285 A1   5/2019   Nye et al.
(Continued)

FOREIGN PATENT DOCUMENTS

CN    112163407 A  *  1/2021   ........... G06F 40/166
CN    113658683 A  *  11/2021
(Continued)

OTHER PUBLICATIONS

International Search Report and Written Opinion in related international application No. PCT/US2022/050704 issued on Feb. 15, 2023.
(Continued)

*Primary Examiner* — Shreyans A Patel
(74) *Attorney, Agent, or Firm* — Polsinelli, P.C.

(57) ABSTRACT

Described are techniques for processing text data. A process can include obtaining an input text data indicative of pathologies associated with a corresponding radiological image. A BERT-based machine learning network can be used to generate a plurality of location tags, each location tag associated with a sentence of input text data and indicative of an anatomical location in the corresponding radiological image. A plurality of sentence groups can be generated using the input text data and the plurality of location tags, each sentence group including sentences of input text data that are associated with a location tag indicative of the same anatomical location. A multi-task learning (MTL)-based machine learning network can be used to generate a plurality of sets of features, each set of features generated based on a particular sentence group and indicative of pathology severity predictions determined for the anatomical location associated with the particular sentence group.

20 Claims, 5 Drawing Sheets

(51) Int. Cl.
*G06F 40/58* (2020.01)
*G06N 3/00* (2023.01)
*G16H 10/60* (2018.01)

(56) References Cited

U.S. PATENT DOCUMENTS

2020/0286294 A1* 9/2020 Musara .................. G16H 50/30
2020/0334416 A1* 10/2020 Vianu .................. G06V 10/764

FOREIGN PATENT DOCUMENTS

| DE | 212015000240 U1 * | 7/2017 | ......... G06F 16/5866 |
| WO | WO-2017151757 A1 * | 9/2017 | |
| WO | WO-2019160557 A1 * | 8/2019 | ............... G06N 3/08 |

OTHER PUBLICATIONS

International Preliminary Report on Patentability in related international application No. PCT/US2022/050704 issued on May 2, 2024.

* cited by examiner

MULTI-TASK ADAPTERS AND TASK SIMILARITY FOR EFFICIENT EXTRACTION OF PATHOLOGIES FROM MEDICAL REPORTS

CROSS-REFERENCE TO RELATED APPLICATIONS

This application claims the benefit of priority to U.S. Provisional Patent Application No. 63/283,006 filed Nov. 24, 2021 and entitled "MULTI-TASK ADAPTERS AND TASK SIMILARITY FOR EFFICIENT EXTRACTION OF PATHOLOGIES FROM MEDICAL REPORTS," the disclosure of which is herein incorporated by reference in its entirety.

TECHNICAL FIELD

The present disclosure relates generally to computer-implemented machine learning systems and methods for analyzing text, and more specifically pertains to natural language understanding of radiology reports.

BACKGROUND

In present healthcare practices, digital images and written reports often serve as a basis of diagnostic assessment. Radiology is one example of a field in which images of patient anatomy, along with dictated and/or written records of assessment by radiologists, often serve as core records reflecting a diagnosis. For example, pathology detection and grading processes are often performed in the context of radiological and/or diagnostic imaging, in which case an MRI or other medical image can be reviewed for any pathologies that are present (e.g., central canal stenosis of the lumbar spine) and a severity grade can then be assigned to each detected pathology (e.g., on a 1-3 or other scale). The process of reviewing medical images to detect and grade pathologies is often performed manually, e.g., by one or more radiologists.

However, the interpretation of digital images is often complex, requiring significant medical and anatomical knowledge as well as an ability to detect subtle or complicated patterns of information in the correct context, and therefore the radiology field has a non-zero error rate. Some diagnostic errors result from deficiencies in a radiologist's skill in interpreting image data, other diagnostic errors result from differences in the communication of diagnostic information in written or dictated diagnostic reports. It is commonplace for different radiology practitioners to express a diagnosis in multiple different ways in writing, or with arcane or incorrect terms; some of these variations will correctly express a patient's diagnosis and some will convey an erroneous or misleading diagnosis.

Therefore, there is a long-felt need in the field for a standardized, robust, and quantitative method for assessing the accuracy of patients' diagnoses and the diagnostic accuracy and error rates achieved by radiology providers. However, this requires a scalable system for standardizing multiple aspects of the diagnostic quality assessment process, including, (1) the diagnostic interpretation of image data, (2) the documentation of diagnostic findings in dictated or written diagnostic reports, and (3) the categorization of various diagnostic errors and quality issues.

While extensive medical records are usually developed for each patient in digital electronic form, typically much of the data is unstructured; examples are the digital medical images and dictated diagnostic reports, both of which are non-standardized across patient exams and not readily interpretable by machines or computers. While more structured dictation could be provided, it is an imperfect approach that is unlikely to be adopted on a widespread basis. Additional tools or systems are needed to more efficiently transform the unstructured information in medical images and/or diagnostic reports into standardized data that can be leveraged for assessment of diagnostic accuracy, error rates, and quality.

SUMMARY

Disclosed are systems and methods for using multi-task adapters and task similarity for the efficient extraction of pathology and/or severity information from medical reports. In some examples, medical reports can include radiologists' reports, which can be obtained from various different radiology practices, most (if not all) of which might employ different writing styles or conventions to describe pathology and severity information. It can therefore be challenging to collect and parse radiologists' notes in an automated fashion. In some cases, radiologists' notes and other medical reports can be used to generate training data for training one or more machine learning networks to perform natural language processing (NLP) or natural language understanding (see e.g., commonly owned U.S. patent application Ser. No. 16/849,506, the contents of which are herein incorporated by reference in their entirety). When generating training data from radiologists' notes, the complexities and difficulties associated with collecting and annotating sufficient amounts of data to cover a broad range of semantics and pathologies can become even more pronounced.

Accordingly, it would be desirable to obtain NLP systems for analyzing medical reports and radiologists' notes, wherein such NLP systems are robust and can be trained quickly using relatively few labeled data points. One such approach, as disclosed herein, trains and deploys one model per body part, and subsequently utilizes a multi-task learning (MTL) approach based on task similarity to modify or update the pre-trained base model to obtain pathology-specific models that can be applied to downstream tasks. By contrast, under existing approaches, separate machine learning/classifier models must be individually trained and deployed for each different pathology and/or downstream task—which can quickly create very large computational and deployment costs, especially as the number of different pathologies (and the number of different pathologies per body part) increases. In some embodiments, the MTL-based approaches and models described herein can achieve similar or otherwise competitive performance to existing pathology-specific models at a significantly reduced computational and deployment cost, e.g., based at least in part on analyzing the cooperative nature of tasks to leverage task similarity.

Systems, apparatuses, processes (also referred to as methods), and computer-readable media (collectively referred to as "systems and techniques") are described herein that can be used to process text data, including radiological reports and/or radiological report text. According to at least one illustrative example, a method is provided, the method comprising: obtaining an input text data indicative of one or more pathologies associated with a corresponding radiological image, wherein the one or more pathologies are included in a plurality of pathologies; generating, using a Bidirectional Encoder Representations from Transformers (BERT)-based machine learning network, a plurality of location tags associated with the input text data, wherein each respective location tag of the plurality of location tags is associated with a sentence included in the input text data and is indicative of an anatomical location of a plurality of anatomical locations in the corresponding radiological image; generating a plurality of sentence groups based on the input text data and the plurality of location tags, wherein each sentence group of the plurality of sentence groups includes one or more sentences that are included in the input text data and are associated with a respective location tag indicative of a same respective anatomical location; and generating, using a multi-task learning (MTL)-based machine learning network, a plurality of sets of features, wherein each set of features of the plurality of sets of features: is generated based on a particular sentence group of the plurality of sentence groups; and is indicative of a plurality of pathology severity predictions determined for the respective anatomical location associated with the particular sentence group.

In another example, an apparatus for processing image data is provided that includes a memory (e.g., configured to store data, such as virtual content data, one or more images, etc.) and one or more processors (e.g., implemented in circuitry) coupled to the memory. The one or more processors are configured to and can: obtain an input text data, the input text data indicative of one or more pathologies associated with a corresponding radiological image, wherein the one or more pathologies are included in a plurality of pathologies; generate, using a Bidirectional Encoder Representations from Transformers (BERT)-based machine learning network, a plurality of location tags associated with the input text data, wherein each respective location tag of the plurality of location tags is associated with a sentence included in the input text data and is indicative of an anatomical location; generate a plurality of sentence groups based on the input text data and the plurality of location tags, wherein each sentence group of the plurality of sentence groups includes one or more sentences that are included in the input text data and are associated with a respective location tag indicative of a same respective anatomical location; and generate, using a multi-task learning (MTL)-based machine learning network, a plurality of sets of features, wherein each set of features of the plurality of sets of features: is generated based on a particular sentence group of the plurality of sentence groups; and is indicative of a plurality of pathology severity predictions determined for the respective anatomical location associated with the particular sentence group.

In another example, a non-transitory computer-readable medium is provided that has stored thereon instructions that, when executed by one or more processors, cause the one or more processors to: obtain an input text data, the input text data indicative of one or more pathologies associated with a corresponding radiological image, wherein the one or more pathologies are included in a plurality of pathologies; generate, using a Bidirectional Encoder Representations from Transformers (BERT)-based machine learning network, a plurality of location tags associated with the input text data, wherein each respective location tag of the plurality of location tags is associated with a sentence included in the input text data and is indicative of an anatomical location; generate a plurality of sentence groups based on the input text data and the plurality of location tags, wherein each sentence group of the plurality of sentence groups includes one or more sentences that are included in the input text data and are associated with a respective location tag indicative of a same respective anatomical location; and generate, using a multi-task learning (MTL)-based machine learning network, a plurality of sets of features, wherein each set of features of the plurality of sets of features: is generated based on a particular sentence group of the plurality of sentence groups; and is indicative of a plurality of pathology severity predictions determined for the respective anatomical location associated with the particular sentence group.

In another example, an apparatus is provided, the apparatus including: means for obtaining an input text data indicative of one or more pathologies associated with a corresponding radiological image, wherein the one or more pathologies are included in a plurality of pathologies; means for generating, using a Bidirectional Encoder Representations from Transformers (BERT)-based machine learning network, a plurality of location tags associated with the input text data, wherein each respective location tag of the plurality of location tags is associated with a sentence included in the input text data and is indicative of an anatomical location of a plurality of anatomical locations in the corresponding radiological image; means for generating a plurality of sentence groups based on the input text data and the plurality of location tags, wherein each sentence group of the plurality of sentence groups includes one or more sentences that are included in the input text data and are associated with a respective location tag indicative of a same respective anatomical location; and means for generating, using a multi-task learning (MTL)-based machine learning network, a plurality of sets of features, wherein each set of features of the plurality of sets of features: is generated based on a particular sentence group of the plurality of sentence groups; and is indicative of a plurality of pathology severity predictions determined for the respective anatomical location associated with the particular sentence group.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. The use of a same reference numbers in different drawings indicates similar or identical items or features. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1A:
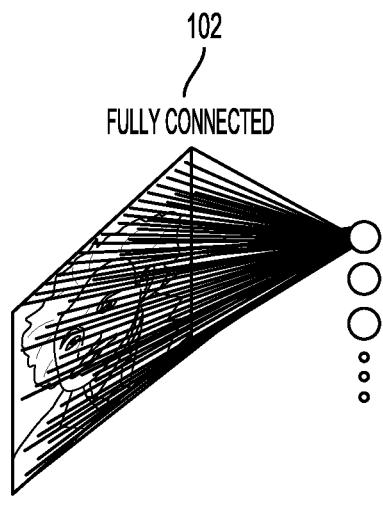
FIG. 1A illustrates an example of a fully connected neural network, in accordance with some examples.

Various embodiments of the disclosure are discussed in detail below. While specific implementations are discussed, it should be understood that this is done for illustration purposes only. A person skilled in the relevant art will recognize that other components and configurations may be used without departing from the spirit and scope of the disclosure. Additional features and advantages of the disclosure will be set forth in the description which follows, and in part will be obvious from the description, or can be learned by practice of the herein disclosed principles. It will be appreciated that for simplicity and clarity of illustration, where appropriate, reference numerals have been repeated among the different figures to indicate corresponding or analogous elements. The description is not to be considered as limiting the scope of the embodiments described herein.

Overview

A neural network is an example of a machine learning system, and can include an input layer, one or more hidden layers, and an output layer. Data is provided from input nodes of the input layer, processing is performed by hidden nodes of the one or more hidden layers, and an output is produced through output nodes of the output layer. Deep learning networks typically include multiple hidden layers. Each layer of the neural network can include feature maps or activation maps that can include artificial neurons (or nodes). A feature map can include a filter, a kernel, or the like. The nodes can include one or more weights used to indicate an importance of the nodes of one or more of the layers. In some cases, a deep learning network can have a series of many hidden layers, with early layers being used to determine simple and low-level characteristics of an input, and later layers building up a hierarchy of more complex and abstract characteristics.

A deep learning architecture may learn a hierarchy of features. If presented with visual data, for example, the first layer may learn to recognize features, such as edges, in the input stream. In another example, if presented with auditory data, the first layer may learn to recognize spectral power in specific frequencies. The second layer, taking the output of the first layer as input, may learn to recognize features, such as shapes for visual data or combinations of sounds for auditory data. For instance, higher layers may learn to represent complex shapes in visual data or words in textual data. Still higher layers may learn to recognize common visual objects and/or named entities.

Neural networks may be designed with a variety of connectivity patterns. In feed-forward networks, information is passed from lower to higher layers, with each neuron in a given layer communicating to neurons in higher layers. A hierarchical representation may be built up in successive layers of a feed-forward network, as described above. Neural networks may also have recurrent or feedback (also called top-down) connections. In a recurrent connection, the output from a neuron in a given layer may be communicated to another neuron in the same layer. A recurrent architecture may be helpful in recognizing patterns that span more than one of the input data chunks that are delivered to the neural network in a sequence. A connection from a neuron in a given layer to a neuron in a lower layer is called a feedback (or top-down) connection. A network with many feedback connections may be helpful when the recognition of a high-level concept may aid in discriminating the particular low-level features of an input.

Figure 1B:
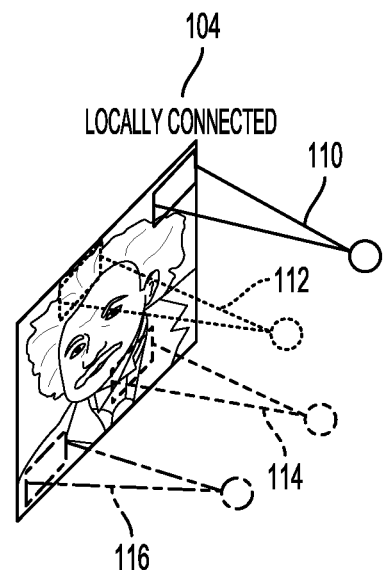
FIG. 1B illustrates an example of a locally connected neural network, in accordance with some examples.

The connections between layers of a neural network may be fully connected or locally connected. FIG. 1A illustrates an example of a fully connected neural network 102. In a fully connected neural network 102, a neuron in a first hidden layer may communicate its output to every neuron in a second hidden layer, so that each neuron in the second layer will receive input from every neuron in the first layer. FIG. 1B illustrates an example of a locally connected neural network 104. In a locally connected neural network 104, a neuron in a first hidden layer may be connected to a limited number of neurons in a second hidden layer. More generally, a locally connected layer of the locally connected neural network 104 may be configured so that each neuron in a layer will have the same or a similar connectivity pattern, but with connections strengths that may have different values (e.g., 110, 112, 114, and 116). The locally connected connectivity pattern may give rise to spatially distinct receptive fields in a higher layer, because the higher layer neurons in a given region may receive inputs that are tuned through training to the properties of a restricted portion of the total input to the network.

Figure 1C:
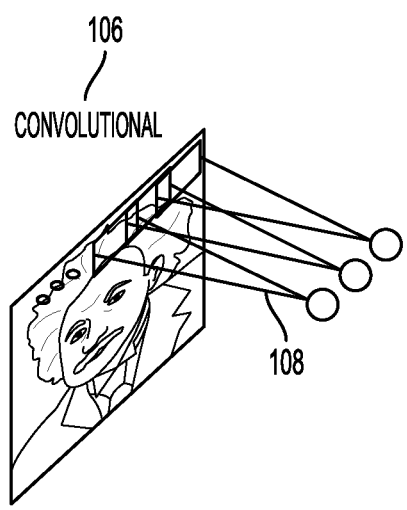
FIG. 1C illustrates an example of a convolutional neural network, in accordance with some examples.

One example of a locally connected neural network is a convolutional neural network. FIG. 1C illustrates an example of a convolutional neural network 106. The convolutional neural network 106 may be configured such that the connection strengths associated with the inputs for each neuron in the second layer are shared (e.g., 108). Convolutional neural networks may be well suited to problems in which the spatial location of inputs is meaningful. Convolutional neural network 106 may be used to perform one or more aspects of video compression and/or decompression, according to aspects of the present disclosure.

Figure 1D:
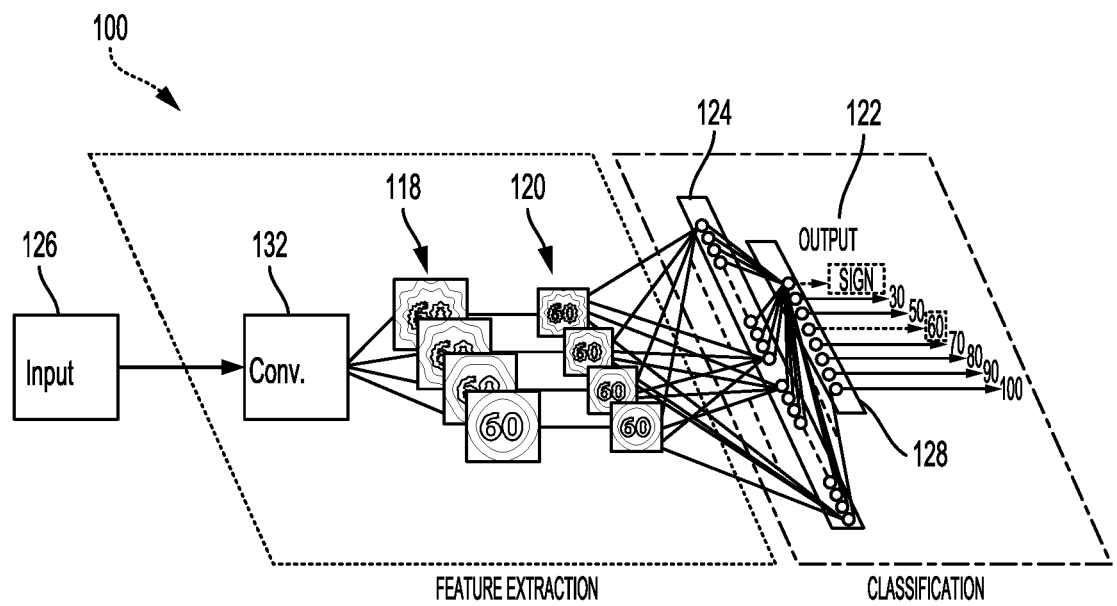
FIG. 1D illustrates a detailed example of a deep convolutional network (DCN) that can be used to recognize features from an image, in accordance with some examples.

One type of convolutional neural network is a deep convolutional network (DCN). FIG. 1D illustrates an example of a DCN 100 designed to recognize features from a given input 126. In some examples, the DCN 100 of the current example may be trained to identify features in the given input 126, such as one or more objects (e.g., in examples in which the given input 126 is an image) and/or one or more named entities (e.g., in examples in which the given input 126 is text data), for example.

In some examples, the DCN 100 may be trained with supervised learning. During training, the DCN 100 may be presented with an input, such as the given input 126, and a forward pass may then be computed to produce an output 122. The DCN 100 may include a feature extraction section and a classification section. Upon receiving the input 126, a convolutional layer 132 may apply convolutional kernels (not shown) to the input 126 to generate a first set of feature maps 118. As an example, the convolutional kernel for the convolutional layer 132 may be a 5×5 kernel that generates 18×28 feature maps. In the present example, because four different feature maps are generated in the first set of feature maps 118, four different convolutional kernels were applied to the input 126 at the convolutional layer 132. The convolutional kernels may also be referred to as filters or convolutional filters.

The first set of feature maps 118 may be subsampled by a max pooling layer (not shown) to generate a second set of feature maps 120. The max pooling layer reduces the size of the first set of feature maps 118. That is, a size of the second set of feature maps 120, such as 14×14, is less than the size of the first set of feature maps 118, such as 18×28. The reduced size provides similar information to a subsequent layer while reducing memory consumption. The second set of feature maps 120 may be further convolved via one or more subsequent convolutional layers (not shown) to generate one or more subsequent sets of feature maps (not shown).

In the example of FIG. 1D, the second set of feature maps 120 is convolved to generate a first feature vector 124. Furthermore, the first feature vector 124 is further convolved to generate a second feature vector 128. Each feature of the second feature vector 128 may include a number that corresponds to a possible feature of the input 126, such as "sign", "60", and "100". A softmax function (not shown) may convert the numbers in the second feature vector 128 to a probability. As such, an output 122 of the DCN 100 is a probability of the input 126 including one or more features.

In the present example, the probabilities in the output 122 for "sign" and "60" are higher than the probabilities of the others of the output 122, such as "30", "40", "50", "70", "80", "90", and "100". Before training, the output 122 produced by the DCN 100 is likely to be incorrect. Thus, an error may be calculated between the output 122 and a target output. The target output is the ground truth of the input 126. The weights of the DCN 100 may then be adjusted so the output 122 of the DCN 100 is more closely aligned with the target output.

To adjust the weights, a learning algorithm may compute a gradient vector for the weights. The gradient may indicate an amount that an error would increase or decrease if the weight were adjusted. At the top layer, the gradient may correspond directly to the value of a weight connecting an activated neuron in the penultimate layer and a neuron in the output layer. In lower layers, the gradient may depend on the value of the weights and on the computed error gradients of the higher layers. The weights may then be adjusted to reduce the error. This manner of adjusting the weights may be referred to as "back propagation" as it involves a "backward pass" through the neural network.

In practice, the error gradient of weights may be calculated over a small number of examples, so that the calculated gradient approximates the true error gradient. This approximation method may be referred to as stochastic gradient descent. Stochastic gradient descent may be repeated until the achievable error rate of the entire system has stopped decreasing or until the error rate has reached a target level. After learning, the DCN may be presented with new inputs (e.g., new images, new text data, etc.) and a forward pass through the network may yield an output 122 that may be considered an inference or a prediction of the DCN.

Deep belief networks (DBNs) are probabilistic models comprising multiple layers of hidden nodes. DBNs may be used to extract a hierarchical representation of training data sets. A DBN may be obtained by stacking up layers of Restricted Boltzmann Machines (RBMs). An RBM is a type of artificial neural network that can learn a probability distribution over a set of inputs. Because RBMs can learn a probability distribution in the absence of information about the class to which each input should be categorized, RBMs are often used in unsupervised learning. Using a hybrid unsupervised and supervised paradigm, the bottom RBMs of a DBN may be trained in an unsupervised manner and may serve as feature extractors, and the top RBM may be trained in a supervised manner (on a joint distribution of inputs from the previous layer and target classes) and may serve as a classifier.

Deep convolutional networks (DCNs) are networks of convolutional networks, configured with additional pooling and normalization layers. DCNs can achieve high performance on many tasks. DCNs can be trained using supervised learning in which both the input and output targets are known for many exemplars and are used to modify the weights of the network by use of gradient descent methods.

DCNs may be feed-forward networks. In addition, as described above, the connections from a neuron in a first layer of a DCN to a group of neurons in the next higher layer are shared across the neurons in the first layer. The feed-forward and shared connections of DCNs may be exploited for fast processing. The computational burden of a DCN may be much less than, for example, that of a similarly sized neural network that comprises recurrent or feedback connections.

The processing of each layer of a convolutional network may be considered a spatially invariant template or basis projection. If the input is first decomposed into multiple channels, such as the red, green, and blue channels of a color image, then the convolutional network trained on that input may be considered three-dimensional, with two spatial dimensions along the axes of the image and a third dimension capturing color information. The outputs of the convolutional connections may be considered to form a feature map in the subsequent layer, with each element of the feature map (e.g., 120) receiving input from a range of neurons in the previous layer (e.g., feature maps 118) and from each of the multiple channels. The values in the feature map may be further processed with a non-linearity, such as a rectification, max(0,x). Values from adjacent neurons may be further pooled, which corresponds to down sampling, and may provide additional local invariance and dimensionality reduction.

Figure 2:
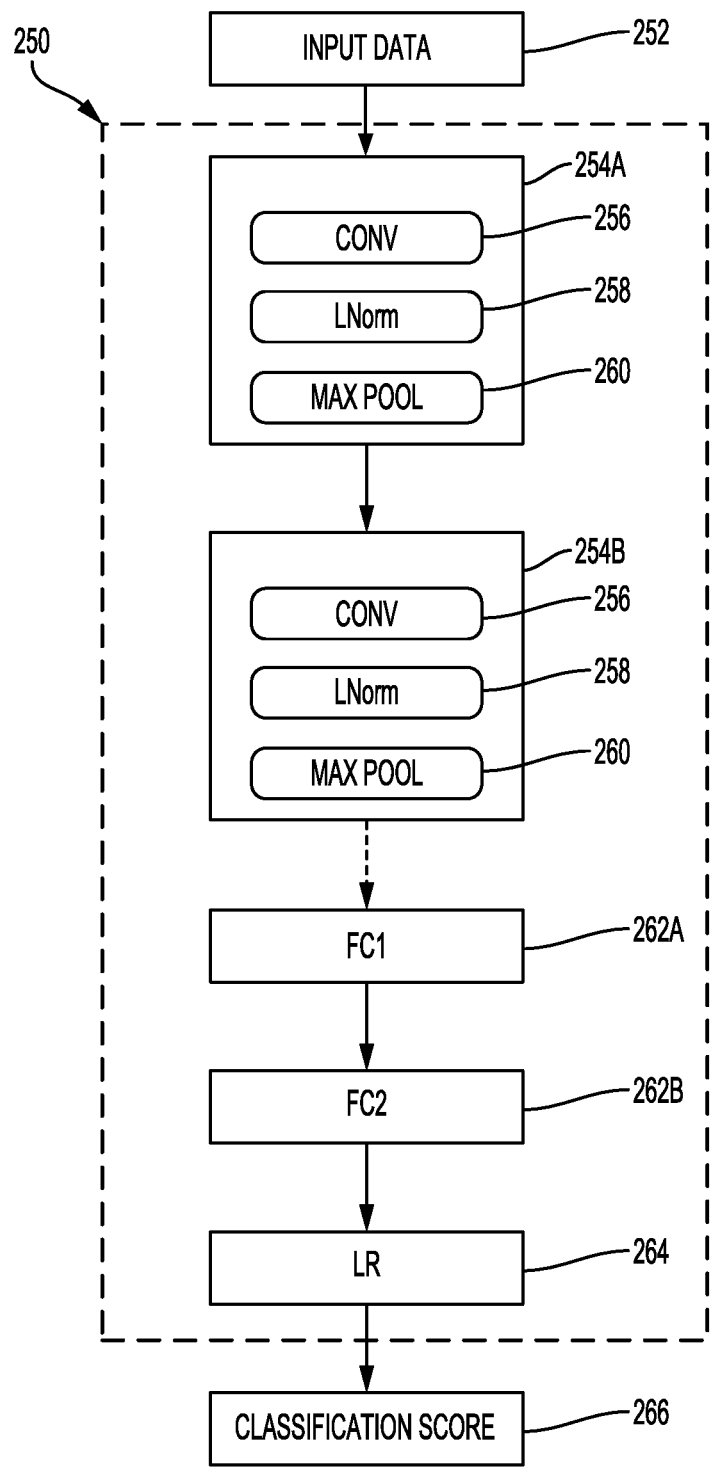
FIG. 2 is a block diagram illustrating another example DCN, in accordance with some examples.

FIG. 2 is a block diagram illustrating an example of a deep convolutional network 250. The deep convolutional network 250 may include multiple different types of layers based on connectivity and weight sharing. As shown in FIG. 2, the deep convolutional network 250 includes the convolution blocks 254A, 254B. Each of the convolution blocks 254A, 254B may be configured with a convolution layer (CONV) 256, a normalization layer (LNorm) 258, and a max pooling layer (MAX POOL) 260.

The convolution layers 256 may include one or more convolutional filters, which may be applied to the input data 252 to generate a feature map. Although only two convolution blocks 254A, 254B are shown, the present disclosure is not so limiting, and instead, any number of convolution blocks (e.g., blocks 254A, 254B) may be included in the deep convolutional network 250 according to design preferences. The normalization layer 258 may normalize the output of the convolution filters. For example, the normalization layer 258 may provide whitening or lateral inhibition. The max pooling layer 260 may provide down sampling aggregation over space for local invariance and dimensionality reduction.

The parallel filter banks, for example, of a deep convolutional network may be loaded on a CPU 102 or GPU 104 of an image processing system 100 to achieve high performance and low power consumption. In some examples, the parallel filter banks may be loaded on the DSP 106 or an ISP 116 of an image processing system 100. The deep convolutional network 250 may access other processing blocks that may be present on the image processing system 100.

The deep convolutional network 250 may include one or more fully connected layers, such as layer 262A (labeled "FC1") and layer 262B (labeled "FC2"). The deep convolutional network 250 may include a logistic regression (LR) layer 264. Between each layer 256, 258, 260, 262, 264 of the deep convolutional network 250 are weights (not shown) that are to be updated. The output of each of the layers (e.g., 256, 258, 260, 262, 264) may serve as an input of a succeeding one of the layers (e.g., 256, 258, 260, 262, 264) in the deep convolutional network 250 to learn hierarchical feature representations from input data 252 (e.g., images, audio, video, sensor data and/or other input data) supplied at the first of the convolution blocks 254A. The output of the deep convolutional network 250 is a classification score 266 for the input data 252. The classification score 266 may be a set of probabilities, where each probability is the probability of the input data including a feature from a set of features.

Another type of neural network is an autoencoder. An autoencoder can be trained (e.g., using training data and one or more loss functions) to receive input and to generate a version of that input at its output (e.g., to essentially copy its input to its output). An autoencoder can be trained to learn efficient data codings in an unsupervised manner. For example, given an image of an object, an autoencoder can first encode the image into a lower dimensional latent representation, and can then decode the latent representation back to an image of the object. An autoencoder can learn (e.g., through training) to compress the input data while minimizing the reconstruction error.

EXAMPLE EMBODIMENTS

A transformer is a type of deep learning model that utilizes an attention mechanism to differentially weight the significance of each part of a given input data and model long-range dependencies. For example, transformers can use the attention mechanism to determine global dependencies between input and output sequences. While transformers are often used to handle sequential input data (e.g., such as text and natural language), a transformer does not necessarily process the data in the same sequential order in which the data was originally received or arranged. Moreover, because transformers can use attention to determine contextual relationships between sub-portions of the input data, a transformer can process some or all of the sub-portions in parallel, such as when computing attention or self-attention.

A transformer may utilize an encoder-decoder architecture. The encoder can include a plurality of encoder layers to process an input sequence iteratively, one layer after another. The decoder can include a plurality of decoder layers to process the encoder output sequence iteratively, one layer after another (e.g., the encoder output is provided as an input to the decoder). Each encoder and decoder layer can include an attention mechanism. For each portion of an input, attention can be used to weight the relevance of every other portion of the input and generate a corresponding output. Decoder layers can include an additional attention mechanism that utilizes information from decoder output(s) at previous time steps. For example, a decoder layer can include an attention mechanism for processing information from decoder outputs at previous time steps, prior to an attention mechanism included in the decoder for processing information from the encodings (e.g., generated by the encoder layer(s)) associated with the current time step.

A transformer can include a feed-forward neural network component in both the encoder and the decoder layers. For example, a feed-forward neural network component can be provided between the attention mechanism included in the encoder layers and the output of the encoder layers, and a feed-forward neural network component can be provided between the attention mechanism included in the decoder layers and the output of the decoder layers. In some examples, the feed-forward neural network may be implemented as a multi-layer perceptron (MLP), among other types of feed-forward neural networks.

In some examples, a transformer can determine attention weights between all tokens simultaneously (e.g., wherein the tokens correspond to features or embeddings, etc.). For example, an attention layer can generate an embedding for each respective token such that the embedding includes (or is otherwise indicative of) information associated with the respective token and a weighted combination of other relevant tokens associated with the respective token. The other relevant tokens associated with the respective token may each be weighted by a corresponding attention weight (e.g., wherein the attention weight is indicative of the weight or strength of the association between the relevant token and the respective token).

An attention layer can be trained to learn three attention weighting matrices, given as a query weights matrix $W_Q$, a key weights matrix $W_K$, and a value weights matrix $W_V$. For each given token i, the corresponding token embedding $x_i$ is multiplied by the three attention weighting matrices to produce a query vector $q_i = x_i W_Q$, a key vector $k_i = x_i W_K$, and a value vector $v_i = x_i W_V$. Attention weights can be determined based on the query vector $q_i$ and the key vector $k_i$. For example, the attention weight $a_{ij}$ from token i to token j can be determined as the dot product between $q_i$ and $k_j$.

Based on the query weights matrix, $W_Q$, and the key weights matrix, $W_K$, being provided as two separate matrices, attention can be non-symmetric. For example, the attention weight $a_{ij}$ can be determined as the dot product $q_i \cdot k_j$ and represents the attention from token i to token j. When attention is non-symmetric, the attention weight $a_{ij}$ can be different than the attention weight $a_{ji}$ (e.g., the attention weight from token j to token i), which can be determined as the dot product $q_j \cdot k_i$.

The output of a transformer attention layer for a given token i is the weighted sum of the value vectors (e.g., $v_i$) of all tokens, weighted by $a_{ij}$, the attention from token i to each of the j additional tokens. For example, an attention layer can determine attention values by computing a matrix of outputs as:

$$\text{Attention}(Q, K, V) = \text{softmax}\left(\frac{QK^T}{\sqrt{d_k}}\right) V$$

Here, the matrix Q is the matrix including all of the i query vectors $q_i$ as row entries; the matrix K is the matrix including all of the i key vectors $k_i$ as row entries; and the matrix V is the matrix including all of the i value vectors $v_i$ as row entries. For example, $Q = W_q \cdot X$; $K = W_k \cdot X$; and $V = W_v \cdot X$. In some aspects, when the inputs to Q, K, V are the same X, the attention computation is a "self" attention. When the inputs to Q, K, V are not the same X, the attention computation is a "cross" attention. For example, self-attention can be determined by using the same embedding sequence X as input to Q, K, and V. Cross-attention can be determined by using a first embedding sequence $X_1$ as input to Q and a second embedding sequence $X_2$ as input to K and V.

The $W_q$, $W_k$, and $W_v$ terms are linear layers that project or map the input vector X to the query (Q), key (K), and value (V) matrices. The term $d_k$ refers to a dimension of a key k, with $\sqrt{d_k}$ acting as a scaling factor. Softmax refers to a softmax function that is used obtain weights on the self-attention values. The layer norm can output the weights to the feedforward neural network component described previously above, as being provided prior to or at the output of the transformer encoder layers and the output of the transformer decoder layers.

Transformers are often utilized in the context of natural language processing (NLP) and/or natural understanding. For example, some NLP approaches are based on pre-trained transformer models that are subsequently fine-tuned (e.g., through an additional training process) on domain-specific corpora. The use of one or more pre-trained transformer models that are later fine-tuned can be useful in scenarios in which there exist multiple tasks on the same given dataset, in which case fine-tuning operations can be performed to generate different models. Finetuning these large transformer models can be computationally expensive, and in some cases, the transformer models may not show significant improvement where there is a lack of training data. To alleviate these problems, a parameter efficient transfer and multitask learning technique can be utilized that ads small networks called Adapters in between various transformer blocks (see, e.g., Neil Houlsby, Andrei Giurgiu, Stanislaw Jastrzebski, Bruna Morrone, Quentin de Laroussilhe, Andrea Gesmundo, Mona Attariyan, and Sylvain Gelly, *Parameter Efficient Transfer Learning for NLP*, 2019; and Jonas Pfeiffer, Andreas Ruckle, Clifton Poth, Aishwarya Kamath, Ivan Vulic, Sebastian Ruder, Kyunghyun Cho, and Iryna Gurevych, *Adapterhub: A Framework for Adapting Transformers*, In Proceedings of the 2020 Conference on Empirical Methods in Natural Language Processing: System Demonstrations, pages 46-54, 2020). In some aspects, Adapter networks (e.g., also referred to as Adapters and/or Adapter modules) can be used to perform more general architectural modifications to re-purpose a pretrained network for a downstream task. For example, in standard fine-tuning, the new top-layer and the original weights are updated. In contrast, in Adapter tuning, the parameters of the original network are frozen and therefore may be shared by many tasks. The adapters described herein can be provided as small bottleneck feedforward layers that are injected between the self-attention and fully connected layer(s) of a transformer machine learning network and after the fully connected layer(s) of the transformer machine learning network. In one illustrative example, an adapter-augmented transformer model may include or otherwise use approximately 8 million trainable parameters (e.g., less than 10% of the pre-trained transformer parameters), which can result in substantial training cost savings.

In some cases, task-specific adapters can also be used to obtain a transformer model that is fine-tuned for a specific task. While approaches based on fine-tuning operations or the use of task-specific adapters can offer efficiency improvements in comparison to individually training a model end-to-end for each specific task, both types of approach are still associated with large computational and deployment costs and overhead.

Systems, apparatuses, processes (also referred to as methods), and computer-readable media (collectively referred to as "systems and techniques") are described herein for performing multi-task learning (MTL)-based pathology classification for textual inputs such as radiological reports. For example, the systems and techniques can be used to provide a multi-task machine learning network that can perform pathology classification for multiple different pathologies (e.g., each pathology classification type representing a different task of the multi-task machine learning network), as will be described in greater depth below.

In some aspects, the systems and techniques described herein can perform multi-task pathology classification using a single MTL-based machine learning network that can exceed or match the performance of multiple task-specific models that are each trained to perform a single one of the multiple tasks (e.g., that are each trained and/or fine-tuned on only one of the multiple tasks). In one illustrative example, the systems and techniques can implement a multitasking BERT-based (Bidirectional Encoder Representations from Transformers) machine learning network. In another illustrative example, the systems and techniques can implement a multitasking BERT-based machine learning network that includes one or more Adapter networks between some (or all) of the BERT output layers.

In some embodiments, the systems and techniques can include or otherwise implement (e.g., as a backbone) a named entity recognition (NER) engine that can be used to perform the multi-task pathology classification of radiological reports. An NER engine can be used to generate structured text data from an input comprising an unstructured (or semi-structured) text data. For instance, an NER engine can be used to locate various named entities that are represented (e.g., mentioned) in a given input text and classify the named entities into pre-defined categories. In the context of input text data that comprises a radiological report, an NER engine can locate and classify named entities into pre-defined categories that are of interest or otherwise relevant to a diagnostic decision. For example, an NER engine can locate and classify named entities within the radiological report text that refer to or represent information indicative of a pathology or abnormality, a corresponding location, a corresponding severity, etc.

In some aspects, the systems and techniques can include or otherwise be based on an NER engine that is the same as or similar to the NER system(s) described in commonly owned U.S. patent application Ser. No. 16/849,506, the disclosure of which is hereby incorporated by reference, although it is appreciated that various other models and/or NER engine implementations can also be utilized without departing from the scope of the present disclosure. For example, the systems and techniques can include an NER engine that is implemented using a BERT-based machine learning network, as mentioned previously. In some aspects, the BERT-based machine learning network can be implemented as a ClinicalBERT machine learning network and/or various other transformer-based machine learning networks that are fine-tuned (e.g., trained) over a dataset of radiological reports and/or clinical terms. ClinicalBERT is a pre-trained BERT model with learned representations from training on a corpus of medical notes and terminology. For example, ClinicalBERT can be pre-trained using a training dataset of patient clinical notes, Electronic Health Records (EHRs), etc. A ClinicalBERT-based machine learning network can include additional learned relationship-based features that are indicative of or associated with the hidden representation(s) of one or more NER spans (e.g., masked NER spans, etc.) and/or the attention weights between NER spans.

Example Training Dataset

In the context of the present disclosure, reference is made to an example training dataset comprising radiological reports (e.g., textual data obtained from radiologists or other medical professionals reading a radiological image) associated with cervical spine pathologies. For example, the radiological reports can be associated with or indicative of a radiologist's read or interpretation of the cervical spine pathologies that are present in a given radiological image of the cervical spine. In some aspects, an input text data (e.g., a radiological report text) can be indicative of one or more clinical findings associated with a corresponding radiological image (e.g., the radiological image from or for which the radiological report text was generated). In some aspects, the example training dataset described below can be used to validate the multi-task and/or task similarity-based approaches implemented by the systems and techniques described herein. However, it is appreciated that this example training dataset (and corresponding pathologies and classification classes) is provided for purposes of illustration and is not intended to be construed as limiting—for example, various other types of training datasets, anatomical features and locations, pathologies, etc., can be utilized without departing from the scope of the present disclosure.

In a radiologist's notes or reports associated with a radiological or other medical image, a radiologist typically discusses the specific (often multiple) pathologies present in the radiological image. The radiologist also usually grades the severity of each identified pathology. Extracting pathologies and/or severity information from a radiological report (e.g., such as a cervical spine report, in the context of the example training dataset) can facilitate the creation of structured databases that can be used for various downstream use cases, which can include but are not limited to cohort creation, quality assessment, and outcome tracking.

The example cervical spine training dataset referred to herein includes radiologists' reports on cervical spine MRI (magnetic resonance imaging) imaging. More particularly, in one illustrative example, the cervical spine training dataset included 1,578 reports obtained from 97 different radiology practices, with each report detailing various pathologies of the cervical spine. A given report may indicate no pathologies are present, that one pathology is present, or that multiple pathologies are present. For example, provided below is an example of a radiological report associated with a medical image of the cervical spine:

"There is mild reversal of cervical lordosis. The vertebral body heights are maintained. No marrow signal abnormalities are identified. Cerebellar tonsils extend up to 2 mm below the foramen magnum on the right. There is no significant crowding at the foramen magnum. Findings are felt most consistent with benign cerebellar tonsillar ectopia. Visualized portions of the posterior cranial fossa and brainstem are otherwise unremarkable. The spina cord is normal in caliber and signal intensity within the imaged field-of-view. Paravertebral and paraspinal soft tissues are grossly unremarkable. C1-C2: Intact dens. No spinal canal stenosis. C2-C3: Maintained disc space with mild disc degeneration. No spinal canal stenosis or neural foraminal narrowing. C3-C4: Maintained disc space with mild disc degeneration. Mild disc bulging that impresses on the anterior thecal sac. No significant spinal canal stenosis or neural foraminal narrowing. C4-C5: Maintained disc space with mild disc desiccation. Uncovertebral degenerative changes. No significant spinal canal or neuroforamina."

Ground truth annotated (e.g., labeled) training data can be generated for each radiological report included in the training dataset. For example, each radiological report can be reviewed and annotated (e.g., labeled) by one or more expert radiologists (e.g., reviewing radiologists). Although a variety of different pathologies can be present in the cervical spine, the training data annotation can be performed over a pre-determined set of the possible pathologies and/or possible severity grades for the pathologies. For example, the cervical spine training dataset described herein can be generated with annotations corresponding to four of the common pathologies that may be present in the cervical spine—central canal (spinal) stenosis, neural foraminal stenosis, disc herniation, and cord compression. It is noted that a greater number of pathologies could be utilized in the training dataset without departing from the scope of the present disclosure, and that the example of four pathologies is used for purposes of clarity of explanation.

In addition to including one or more pathology labels, each respective radiological report included in the annotated training data can further include one or more severity or grading labels. For example, each of the four pathologies of the cervical spine, as noted above, can be associated with a severity grade and/or otherwise grouped into different severity categories. In some examples, the set of severity or grading labels can be the same for each of the different pathology classifications. In some examples, the set of severity or grading labels may vary for different pathology classifications. Table 1, below, depicts example statistics of the example labeled training dataset corresponding to 1,578 radiological reports for cervical spine medical imaging, wherein each radiological report can be associated with one or more of the pathology classification labels "Stenosis," "Disc," "Cord," or "Foraminal" and each pathology classification label can be associated with a corresponding severity label "None," "Mild/Moderate," or "Severe":

TABLE 1

Statistics of example cervical spine training dataset.

| Split | Stenosis | Disc | Cord | Foraminal |
|---|---|---|---|---|
| Train | None: 5488 Mild/ Moderate: 561 Severe: 178 | None: 2731 Mild/ Moderate: 2699 Severe: 797 | None: 5702 Mild/ Severe: 525 | None: 5262 Mild/ Severe: 965 |
| Test | None: 793 Mild/ Moderate: 68 Severe: 19 | None: 401 Mild/ Moderate: 378 Severe: 101 | None: 806 Mild/ Severe: 74 | None: 789 Mild/ Severe: 91 |

Multi-Task Learning (MTL)-Based Machine Learning Network

Continuing in the example above, in which radiological reports are obtained for cervical spine MRI or other medical images, one or more machine learning networks (e.g., models) can be trained and used to determine one or more pathologies that are present in a given input radiological report, and to determine a corresponding severity grade associated with each detected pathology. As mentioned previously, existing approaches may perform multiple pathology classification tasks by using multiple different task-specific machine learning networks (e.g., when a given input can be associated with multiple different pathologies, each pathology classification is represented as its own class and uses its own task-specific machine learning network). The systems and techniques described herein can represent each pathology classification as a task that is included in a single multi-task learning (MTL) episode, as will be described in greater depth below.

For example, given the four example pathologies of the example cervical spine training dataset, multiple tasks can be created for a given radiological report, where each task is to predict the severity of a pathology that is identified for a given motion segment (e.g., the smallest physiological motion unit of the spinal cord). In some cases, breaking information down by motion segment level can enable pathological findings to be correlated with clinical exam findings, and moreover, could be used to inform future treatment interventions.

Treating each pathology classification task of the multiple pathology classification tasks separately can be inefficient. For example, given the semantic similarities between the set of pathology classifications that may be associated with the same given radiological report (e.g., the pathology classifications may be semantically similar because the given radiological report can refer to a radiological image of a particular body part or anatomical region, such as the cervical spine) and given the possible co-occurrence of multiple pathologies in a same sentence of the radiological report, the multiple tasks that are created for a given radiological report can be similar.

Based at least in part on this similarity, it is contemplated herein that an MTL (multi-task learning) approach can be provided that uses a single MTL-based machine learning network to perform all of the pathology classification tasks, while substantially matching or exceeding the performance of existing task-specific approaches that use one task-specific machine learning network per pathology classification task. In one illustrative example, a task similarity can be determined between the multiple pathology classification tasks that may be associated with a given radiological report, based at least in part on the Wasserstein distance (and/or a Wasserstein distance approximation) between the tasks, as will be explained in greater depth below. Notably, in comparison to existing task-specific models, the presently disclosed MTL-based approach can reduce hardware requirements for training and moreover, can be faster in inference time.

Multi-task learning (MTL) is a machine learning approach in which multiple learning and/or inference tasks can be performed at the same time, while exploiting commonalities and differences across tasks. MTL-based approaches can leverage the domain-specific information included or represented in the training signals of related tasks. For example, in some cases, based on sharing representations between related tasks, an MTL-based approach can better generalize on an original task and/or across the multiple related tasks. An MTL-based approach can be applied to different machine learning models, networks, tasks, etc. For example, MTL can be applied in the context of Natural Language Processing (NLP), as will be described in greater depth below.

In an MTL-based approach, information can be shared across some or all of the tasks. This information sharing can be based on one or more task groupings, which can be pre-determined and/or can themselves be learned. More generally, it is contemplated that in an MTL approach, information can be selectively shared across the tasks depending on the structure or nature of the underlying task relatedness. Determining this task relatedness, or otherwise determining the task grouping(s) that will be used, can therefore be a factor in the performance of machine learning models and networks using MTL-based approaches.

Figure 3:
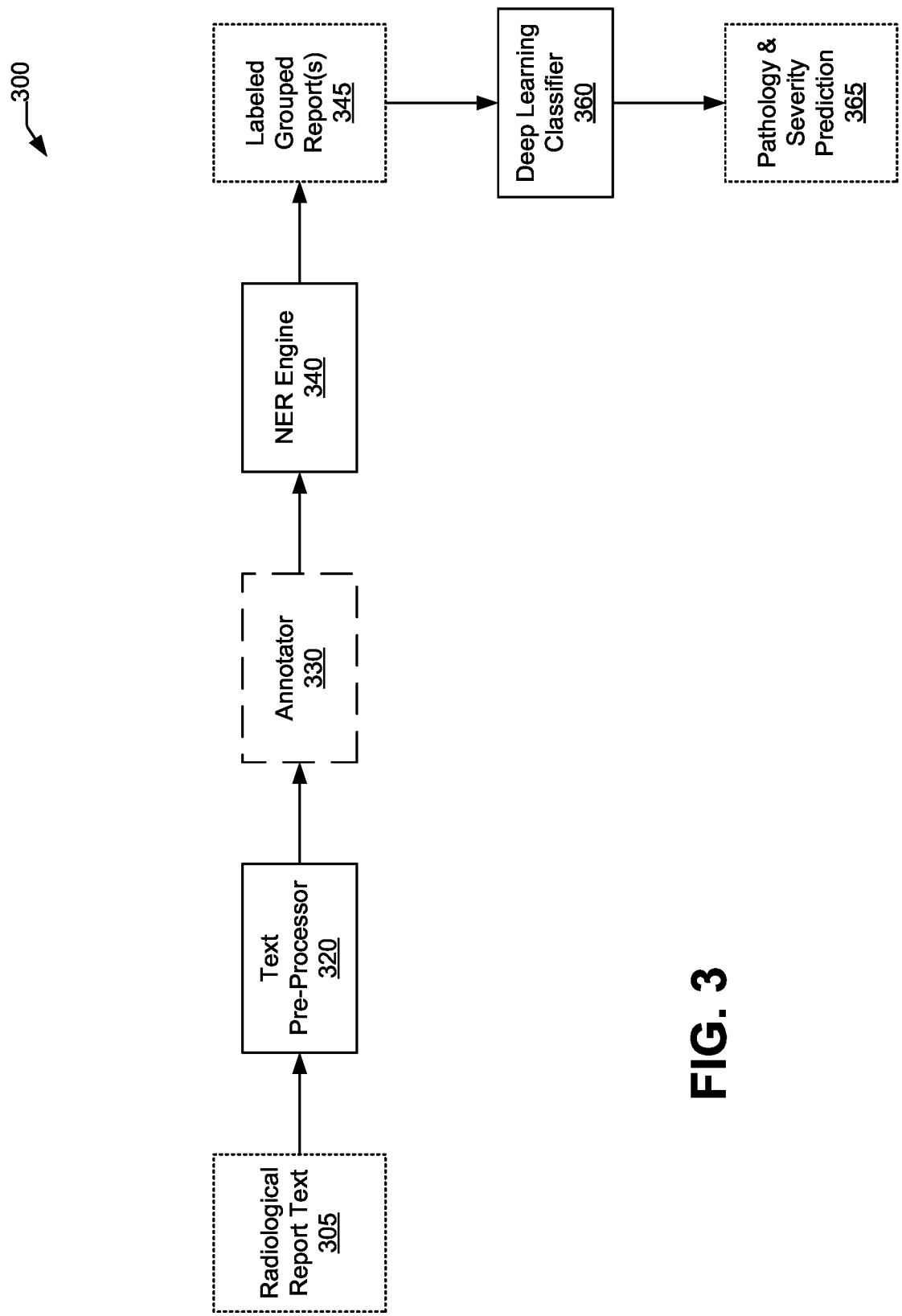
FIG. 3 is a diagram illustrating an example architecture that can be used to implement one or more MTL-based machine learning networks for multi-task pathology classification for a radiological report input, in accordance with some examples.

FIG. 3 is a diagram illustrating an example architecture 300 that can be used to implement one or more MTL-based machine learning networks for multi-task pathology classification for a radiological report input. For example, the architecture 300 can receive as input one or more radiological report texts 305, which may be the same as or similar to the radiological reports (e.g., radiologists' reports) described above. The input radiological report text 305 can be provided to a text pre-processor 320, which can perform operations that may include, but are not limited to, segmentation of the input radiological report text 305, parsing of the input radiological report text 305, error correction of the input radiological report text 305, optical character recognition (OCR) of the input radiological report text 305, normalization of the input radiological report text 305, etc.

The input radiological report text 305 can be provided or obtained as a training data sample (e.g., when architecture 300 is used to perform MTL-based training of a machine learning network) or an inference input (e.g., when architecture 300 is used to perform multi-task classification for an input report). In examples where architecture 300 is used to perform MTL-based training, the architecture 300 may, in some embodiments, include an annotator 330. The annotator 330 can receive as input the pre-processed radiological report text from text pre-processor 320, which is un-labeled text data. Annotator 330 can apply one or ground-truth labels to generate as output a labeled (e.g., annotated) ground-truth training data sample for the input radiological report text 305. The labeled ground-truth training data sample generated by annotator 330 can subsequently be provided as input to an NER engine 340.

In examples where architecture 300 is used to perform inference, annotator 330 can be removed or otherwise not included in the architecture 300, such that the pre-processed radiological report text output by the text pre-processor 320 is provided as input to an NER engine 340.

As mentioned previously, an NER engine (e.g., such as NER engine 340) can be used to generate structured text data from an input comprising an unstructured (or semi-structured) text data. For instance, NER engine 340 can be used to detect various named entities that are represented (e.g., mentioned) in a given input text and classify the named entities into pre-defined categories. A named entity can be one word or multiple words, within contiguous spans of words, that refer to the same semantic concept, object, entity, etc. In some aspects, each pathology classification associated with the multi-task machine learning network can be considered a category of information, or named entity, that can be captured by multiple words within contiguous spans of words. For example, "Central Canal Stenosis" is a three-word span that represents a single pathology, while the abbreviation "C Canal Stenosis" is a different three-word span that represents the same single pathology (e.g., and similarly, the misspelling "Central Cannal Stenoses" would be another example of a different three-word span that represents the same single pathology, etc.).

In the context of input text data that comprises a radiological report (e.g., input 305), NER engine 340 can locate and/or classify named entities into pre-defined categories that are of interest or otherwise relevant to a diagnostic decision. In one illustrative example, NER engine 340 can locate and classify named entities within the radiological report text that refer to or represent information indicative of an anatomical location. For example, NER engine 340 can locate and group (e.g., classify) portions of the radiological report text that refer to the different motion segments of the cervical spine. In other words, the named entities identified and used to perform grouping by NER engine 340 can be the different motion segments of the spine and/or groups thereof. In one illustrative example, NER engine 340 can predict location tags that are present in each sentence of the input radiological report text 305. Based on predicting the location tags for the input radiological report text 305, subsequent (e.g., downstream) pathology detection and classification (e.g., performed by a deep learning classifier 360) can be performed at the motion segment level.

For example, NER engine 340 can generate as output one or more labeled grouped reports 345 (e.g., when the input radiological report text 305 is an annotated training data sample) or one or more grouped reports 345 (e.g., when the input radiological report text 305 is an un-labeled input provided to the trained machine learning network for inference). In some embodiments, the NER engine 340 can group the sentences of the input radiological report text 305 into different groups based on the predicted location tag determined for each sentence. For instance, NER engine 340 can generate the grouped report 345 to group the sentences of the input radiological report text 305 into different motion segment groups, such as C2-C3, C3-C4, C4-C5, C5-C6, C6-C7, and C7-T1.

In some aspects, the systems and techniques can include or otherwise be based on an NER engine that is the same as or similar to the NER system(s) described in commonly owned U.S. patent application Ser. No. 16/849,506, the disclosure of which is hereby incorporated by reference, although it is appreciated that various other models and/or NER engine implementations can also be utilized without departing from the scope of the present disclosure.

In some examples, NER engine 340 can be implemented using a BERT-based machine learning network, as mentioned previously. In one illustrative example, NER engine 340 can be implemented as a ClinicalBERT-based machine learning network (e.g., among various other transformer-based machine learning networks that are fine-tuned (e.g., trained) over a dataset of radiological reports and/or clinical terms). In some embodiments, NER engine 340 can be implemented as BERT-based (e.g., ClinicalBERT-based) binary classifier (e.g., Location Tag vs. the Other Tag). In some cases, a ClinicalBERT-based binary classifier used to implement NER engine 340 can be trained for five epochs with a batch size of 16 and a sequence length of 256. In some examples, an AdamW optimizer can be utilized with a weight decay of 1e-4 (e.g., a BERT Adam optimizer, or a weight decoupled Adam optimizer). A learning rate of 1e-5 can be used with a linear learning rate decay scheduler.

In some embodiments, one or more Adapter networks can be used to augment the NER engine 340. For example, one or more Adapter networks can be used to augment the BERT or ClinicalBERT-based machine learning network used to implement NER engine 340. The one or more Adapter networks are also referred to herein as "multi-task Adapters" or "multi-task Adapter networks."

In one illustrative example, Adapters can be provided as two-layer feedforward machine learning networks with a bottle neck dimension of 48. Adapter weights can be initialized such that the whole Adapter layer can be approximated as an identity function, e.g., can be seen as an autoencoder architecture. In some examples, Gaussian Error Linear Unit (GELU) activation functions or Rectified Linear Unit (ReLU) activation functions can be used as non-linearities between the feedforward layers of the Adapter networks.

As mentioned previously, it is contemplated herein that the NER engine 340 can be used to provide efficient extraction of pathologies represented in a given radiological report input text (e.g., input text 305), using a multi-task learning (MTL)-based approach. For instance, by implementing NER engine 340 as a multitasking NER engine (e.g., training NER engine 340 using an MTL-based approach, implementing NER engine 340 using a multitasking BERT/Clinical-BERT-based machine learning model, etc.), at least some (or all) of the learned features of the NER engine 340 can be reused for multiple different tasks. In some embodiments, the reuse of learned features across multiple tasks performed by multi-task NER engine 340 can be based at least in part on a similarity between the respective tasks for which feature reuse is implemented.

Described below are example multitasking frameworks that can be used to implement multi-task NER engine 340 and/or the multi-task machine learning architecture 300 illustrated in FIG. 3. In particular, two example multitasking machine learning frameworks are described: a multitasking BERT-based machine learning network and a multitasking Adapter-augmented BERT-based machine learning network. Subsequently, each of the two example multitasking machine learning frameworks are compared to baseline results that are obtained from fine-tuning a pre-trained ClinicalBERT model on each of the four cervical spine pathology classification tasks. In this example, the four cervical spine pathology classification tasks are again predicting the respective severity of the four most common cervical spine pathologies (e.g., central canal (spinal) stenosis, disc herniation, cord compression, and neural foraminal stenosis). Fine-tuning the pre-trained ClinicalBERT model on each of the above pathology classification tasks therefore results in four BERT-based, task-specific models (e.g., a single tasker baseline).

In one illustrative example, the multi-task NER engine 340 and/or the multi-task machine learning architecture 300 of FIG. 3 can be implemented using a multitasking BERT model. For example, instead of individually fine-tuning four separate BERT-based models, as in the baseline approach, the systems and techniques described herein can implement multi-task NER engine 340 based on applying a separate classifier head (e.g., linear layer) to a pre-trained BERT-based model for each pathology classification task. In some embodiments, the pre-trained BERT model can be the same as or similar to a PubMedBERT/MSRBERT model. PubMedBERT is a BERT model that is pre-trained using abstracts from the PubMed database. In some embodiments, the pre-trained BERT model can be a RADBERT model (Radiological BERT) or a ClinicalBERT model.

For instance, multi-task NER engine 340 can be implemented by applying four separate classifier heads (e.g., four linear layers) to a pre-trained BERT model or a pre-trained ClinicalBERT model. Continuing in the cervical spine example from above, each classifier head can be associated with a respective one of the four different pathology classification tasks or categories.

In some aspects, a pre-trained BERT-based model that includes the four separate classifier heads can have an output layer of shape [3,3,2,2]. More generally, a pre-trained BERT-based model can be extended with a classifier head/linear layer for each of n unique pathology classification categories or pathology classification tasks that are to be associated with the resulting multi-task NER engine 340, with the resulting output layer having a shape (e.g., dimension) of 1×n. In other words, the output layer of the multi-task NER engine 340 can include one or more outputs for each classifier head/unique pathology classification category/unique pathology classification task.

In the example in which the output layer has a shape or dimension of [3,3,2,2], the first set of 3-outputs can correspond to logits for the spinal stenosis severity prediction; the next (e.g., second) set of 3-outputs can correspond to logits for the disc herniation severity prediction; the next (e.g., third) set of 2-outputs can correspond to logits for the cord compression severity prediction; and the final (e.g., fourth) set of 2-outputs can correspond to logits for the foraminal stenosis severity prediction. In some embodiments, a dropout of 0.5 can be added to the BERT vectors before they are fed to the classifier layers.

Each classifier head (e.g., of the four classifier heads) can be trained based on a corresponding cross-entropy loss. For example, given an input radiological report text training data sample (e.g., input text 305), NER engine 340 can determine a set of pathology severity logits that are indicative of a predicted severity of an identified pathology classification. The set of pathology severity logits can be generated and provided as output by the classifier head that is associated with the identified pathology classification. Accordingly, the cross-entropy loss for a given classifier head can be determined as the cross-entropy loss between the predicted pathology severity logits generated by the given classifier head and the corresponding ground truth targets/labels for the input text 305 (e.g., thereby resulting in four separate cross-entropy losses). In one illustrative example, the respective cross-entropy losses determined for each pathology-specific classifier head can be used to obtain a joint loss, $\mathcal{L}$:

$$\mathcal{L} = l_{stenosis} + l_{disc} + l_{cord} + l_{foraminal} \quad \text{Eq. (1)}$$

The joint loss of Eq. (1) can be used to allow the gradients to be back-propagated through the whole model, and the four classifier heads can be trained jointly to yield a trained multitasking BERT model, e.g., by fine-tuning the parameters of the pre-trained BERT or RADBERT model used as input. In other words, the four classifier heads included in multi-task NER engine 340 can be jointly trained using backpropagation based on the joint loss function of Eq. (1).

In some examples, it may be computationally expensive to apply fine-tuning operations to all of the parameters of large transformer models. Additionally, these large transformer models may not show significant improvement when there is a relatively small amount of training data. Accordingly, in some embodiments, one or more parameter efficient transfer and multitask learning techniques can be introduced by adding small Adapter networks between certain transformer blocks of the pre-trained BERT model, as will be described in greater depth below.

For instance, in another illustrative example, the multi-task NER engine 340 and/or the multi-task machine learning architecture 300 of FIG. 3 can be implemented using a multitasking Adapter-augmented BERT model. Adapter networks (also referred to as Adapter blocks or Adapter modules) can be used to perform architectural modifications to repurpose a pre-trained network for a downstream task. Notably, Adapters do not require fine-tuning of all parameters of the pre-trained model, and instead introduce a small number of task-specific parameters—while keeping the underlying pre-trained model (and the parameters thereof) fixed.

For example, in existing and/or conventional fine-tuning operations, both the new top layer weights and the original weights of a given machine learning network are updated. For example, existing fine-tuning operations may be performed by updating the new top layer weights associated with the four classifier heads in the example described above, and by updating the original weights from the pre-trained BERT model (e.g., ClinicalBERT, RADBERT, etc.). By contrast, in Adapter-based tuning, the parameters of the original, pre-trained network are frozen—and therefore can be shared by different tasks.

In some embodiments, a multitasking Adapter-augmented BERT-based machine learning network (e.g., associated with NER engine 340 and/or the architecture 300 illustrated in FIG. 3) can be generated by inserting Adapters in between one or more (or all) of the BERT output layers. In one illustrative example, one or more Adapters can be provided between every BERT output layer. In some aspects, the multitasking Adapter-augmented BERT-based machine learning network can be trained based on freezing the BERT weights during training. For example, the BERT weights can be frozen during training in order to keep the underlying pre-trained model fixed. Notably, the multitasking adapter-augmented BERT model described herein can be configured to use the same Adapter(s) across all tasks, without experiencing negative impacts such as catastrophic forgetting across tasks. This is in contrast to existing architectures that make use of Adapters, in which splitting (e.g., task-specific) and fusion Adapters are needed in order to prevent catastrophic forgetting across tasks.

In some examples, the use of the same Adapter(s) across tasks can be based at least in part on one or more task similarities. For example, in an MTL-based approach, such as those described herein, information can be shared across some or all of the tasks. This information sharing can be based on one or more task groupings, which can be pre-determined and/or can themselves be learned. More generally, it is contemplated that in an MTL approach, information can be selectively shared across the tasks depending on the structure or nature of the underlying task relatedness. Determining this task relatedness, or otherwise determining the task grouping(s) that will be used, can therefore play an important role in the performance of machine learning models and networks using MTL.

In some examples, factors such as task similarity and semantics can be analyzed in order to better understand which tasks should be grouped together and/or to better understand certain conditions that may help MTL to succeed. As disclosed herein, a distance between tasks can be calculated and used to implement improved multitasking models, including multitasking NLP models and multitasking medical NLP models. A task can be represented as a conditional distribution:

$$\tau_{\psi_y}(X) := P(X|Y=y) \quad \text{Eq. (2)}$$

where X is the feature space and Y is the label space.

Based on Eq. (2), the distance between two tasks $\tau_{\psi_y}(X)$ and $\tau_{\psi_{y'}}(X')$ can subsequently be given as:

$$d((X,y),(X',y')) := W_2(\tau_{\psi_y}(X), \tau_{\psi_{y'}}(X')) \quad \text{Eq. (3)}$$

where $W_2$ is the 2-Wasserstein distance (e.g., a metric describing the distance between two distributions). It is noted that in many cases, computing Wasserstein distances can be a highly computationally expensive task. Therefore, in scenarios with constrained computational overhead, the 2-Wasserstein distance $W_2$ can be approximated by various different techniques, e.g., using the Wasserstein-Bures metric or by various entropic regularized Sinkhorn divergences.

As contemplated in the context of the present disclosure, in some embodiments $W_2$ can be approximated by a sliced Wasserstein distance with 60 random projections of dimensions in logspace between 1 and 4. The sliced Wasserstein distance can then be applied to a pretrained, task-specific BERT, such as a pre-trained ClinicalBERT and/or a pre-trained RADBERT machine learning network as described above that may be used to implement the NER engine 340 and/or the machine learning architecture 300 illustrated in FIG. 3.

To apply the sliced Wasserstein distance approximation for $W_2$, embeddings can be extracted from the final BERT layer of the pretrained, task-specific BERT model. In the context of this example, the feature space X can be the 768-dimensional vector representation of the [CLS] classification token coming from the appropriate BERT model. The sliced Wasserstein distances between these BERT embeddings can then be determined, e.g., using Eq. (2) and Eq. (3) above.

For example, Table 2, below, depicts sliced Wasserstein distances between five different classification tasks of a training set built from radiological reports detailing pathologies of the cervical spine (e.g., each classification task is a combination of a pathology and a severity grade):

TABLE 2

Example sliced Wasserstein distances calculated between the conditional distributions of five classification tasks of a training set containing annotated radiological reports on cervical spine pathologies.

| Task | Mild Stenosis | Severe Disc | Mild Disc | Mild/Severe Foraminal | Mild/Severe Cord |
|---|---|---|---|---|---|
| Mild Stenosis | 0 | .7 ± .4 | .3 ± .2 | 1.2 ± .3 | .7 ± .6 |
| Severe Disc | .7 ± .4 | 0 | .2 ± .1 | .8 ± .6 | .6 ± .5 |
| Mild Disc | .3 ± .2 | .2 ± .1 | 0 | .7 ± .5 | 1.1 ± .7 |
| Mild/Severe Foraminal | 1.2 ± .3 | .8 ± .6 | .7 ± .5 | 0 | .8 ± .7 |
| Mild/Severe Cord | .7 ± .6 | .6 ± .5 | 1.1 ± .7 | .8 ± .7 | 0 |

In addition to the sliced Wasserstein distance approximation described above, an upper bound can be determined for the 2-Wasserstein distance $W_2$ of Eq. (3), as follows:

$$W_2(\mathcal{T}_{\psi_y}(X), \mathcal{T}_{\psi_y}(X')) \leq \mathrm{diam}(A) \cdot TV(\mathcal{T}_{\psi_y}(X), \mathcal{T}_{\psi_y}(X')) \quad \text{Eq. (4)}$$

where diam(A) is the diameter of the support of the measures (and in some examples can be bounded by 59.4), and $TV(\mathcal{T}_{\psi_y}(X), \mathcal{T}_{\psi_y}(X'))$ is the total variation and can be bounded by 1.

It is noted that the example sliced Wasserstein distances of Table 2 are all relatively small in value and are also lower than the upper bound given by Eq. (4). The relatively small distances between tasks likely contributes to the ability of the presently disclosed multitask model to substantially match or replicate the performances of conventional task-specific models and can be seen to validate the use of multi-task adapters and MTL based at least in part on task similarity.

Task similarity can be used to drive a determination that a given set of tasks are similar and that the sentences across the tasks have similar structure and semantic meaning. Based on such a determination, either of the example multitasking, BERT-based networks described above can be utilized, and can achieve similar or equal performance to existing task-specific models, without task-specific architecture. The presently disclosed multitasking BERT-based machine learning networks therefore can provide increased efficiency and reduced computational complexity in training, but without sacrificing or otherwise compromising the accuracy or speed of inference.

For example, Table 3 depicts a set of example experimental results (e.g., macro F1 scores) of the multitasking BERT-based machine learning network and the multitasking adapter-augmented BERT-based machine learning network that are disclosed herein. The example experimental results can be seen to substantially match or exceed the performance of the baseline single tasker BERT model as well as BERT models having the adaptations required in existing architectures (e.g., task-specific Adapters and fusion Adapters):

TABLE 3

Example of experimental results (macro F1 scores) comparing the performance of the presently disclosed multitasking BERT model and multitasking adapter-augmented BERT model vs. a baseline single tasker BERT model and BERT models having task-specific Adapters or fusion Adapters.

| Classification Task | Baseline BERT (single tasker) | Multi-tasking BERT | Baseline BERT w/ Task-specific Adapters | Multi-tasking Adapter-augmented BERT | Fusion Adapters |
|---|---|---|---|---|---|
| Stenosis | .65 | .66 | .62 | .63 | .61 |
| Disc | .67 | .69 | .66 | .71 | .68 |
| Cord | .72 | .76 | .71 | .75 | .76 |
| Foraminal | .83 | .82 | .80 | .78 | .81 |

In other words, as can be seen in Table 3, both the multitasking BERT model and the multitasking adapter-augmented BERT model described herein allow the same or better performance to be achieved with only a single model as compared to four separate task-specific models, as is required in existing solutions. Moreover, not only is the ultimate performance matched or exceeded, but the inference time achieved by the presently disclosed multitasking BERT model and the multitasking adapter-augmented BERT model is significantly faster in comparison to any of these three existing solutions:

TABLE 4

Example of experimental results comparing the inference speed (in seconds) of the presently disclosed multitasking BERT model and multitasking adapter-augmented BERT model vs. a baseline single tasker BERT model and a BERT model with task-specific Adapters.

| Model | Baseline BERT (single tasker) | Multitasking BERT | Baseline BERT with Task specific Adapters | Multitasking Adapter Augmented BERT |
|---|---|---|---|---|
| Walltime (seconds) | 259.64 | 56.93 | 281.56 | 60.16 |

Figure 4:
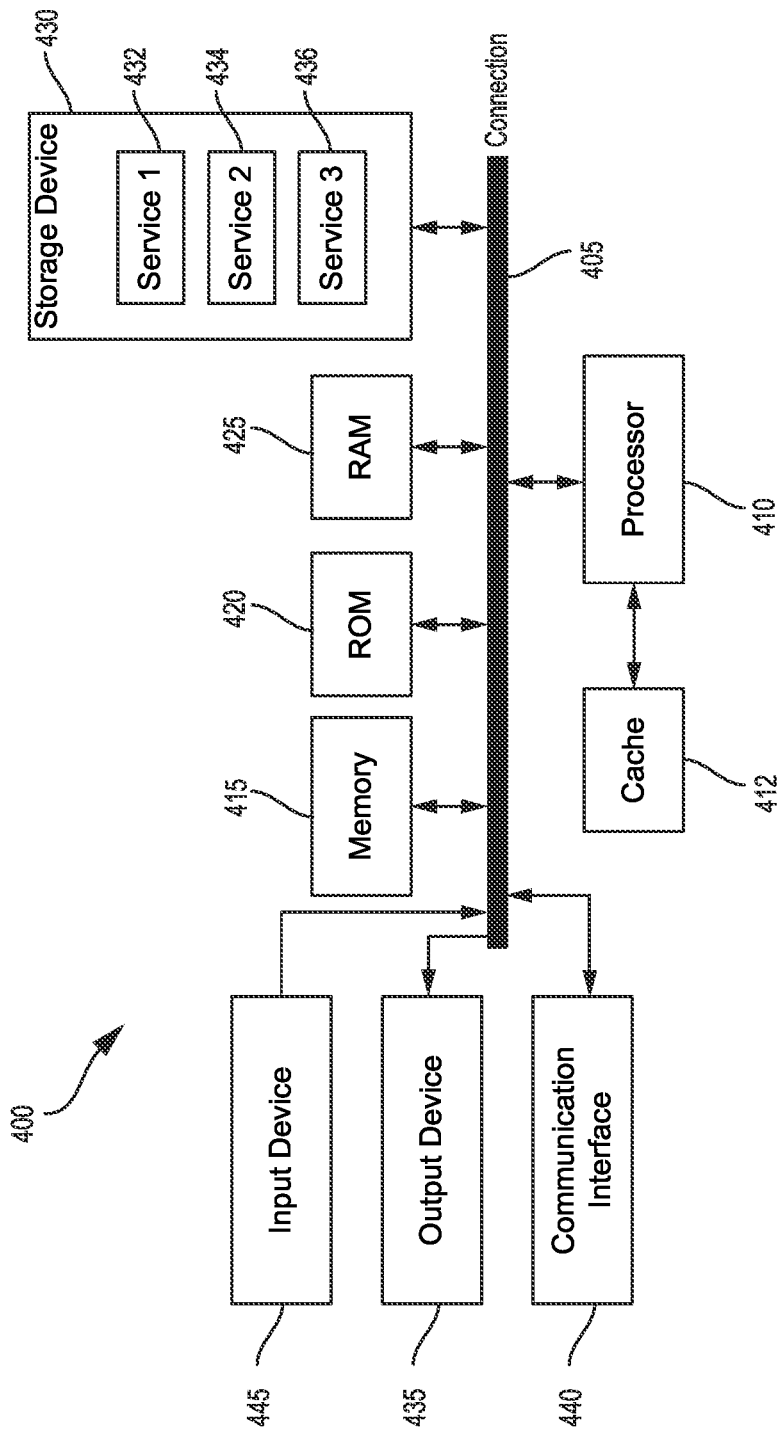
FIG. 4 illustrates an example computing system that can be used to implement various aspects described herein.

FIG. 4 illustrates an example computing device architecture 400 of an example computing device which can implement the various techniques described herein. In some examples, the computing device can include a mobile device, a wearable device, an XR device, a personal computer, a laptop computer, a video server, a video game console, a robotic device, a set-top box, a television, a camera, a server, or other device. For example, the computing device architecture 400 can implement the neural P-frame coding system 800 of FIG. 8. The components of computing device architecture 400 are shown in electrical communication with each other using connection 405, such as a bus. The example computing device architecture 400 includes a processing unit (CPU or processor) 410 and computing device connection 405 that couples various computing device components including computing device memory 415, such as read only memory (ROM) 420 and random access memory (RAM) 425, to processor 410.

Computing device architecture 400 can include a cache of high-speed memory connected directly with, in close proximity to, or integrated as part of processor 410. Computing device architecture 400 can copy data from memory 415 and/or the storage device 430 to cache 412 for quick access by processor 410. In this way, the cache can provide a performance boost that avoids processor 410 delays while waiting for data. These and other modules can control or be configured to control processor 410 to perform various actions. Other computing device memory 415 may be available for use as well. Memory 415 can include multiple different types of memory with different performance characteristics. Processor 410 can include any general purpose processor and a hardware or software service, such as service 1 432, service 2 434, and service 3 436 stored in storage device 430, configured to control processor 410 as well as a special-purpose processor where software instructions are incorporated into the processor design. Processor 410 may be a self-contained system, containing multiple cores or processors, a bus, memory controller, cache, etc. A multi-core processor may be symmetric or asymmetric.

To enable user interaction with the computing device architecture 400, input device 445 can represent any number of input mechanisms, such as a microphone for speech, a touch-sensitive screen for gesture or graphical input, keyboard, mouse, motion input, speech and so forth. Output device 435 can also be one or more of a number of output mechanisms known to those of skill in the art, such as a display, projector, television, speaker device, etc. In some instances, multimodal computing devices can enable a user to provide multiple types of input to communicate with computing device architecture 400. Communication interface 440 can generally govern and manage the user input and computing device output. There is no restriction on operating on any particular hardware arrangement and therefore the basic features here may easily be substituted for improved hardware or firmware arrangements as they are developed.

Storage device 430 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 425, read only memory (ROM) 420, and hybrids thereof. Storage device 430 can include services 432, 434, 436 for controlling processor 410. Other hardware or software modules are contemplated. Storage device 430 can be connected to the computing device connection 405.

In one aspect, a hardware module that performs a particular function can include the software component stored in a computer-readable medium in connection with the necessary hardware components, such as processor 410, connection 405, output device 435, and so forth, to carry out the function.

The term "device" is not limited to one or a specific number of physical objects (such as one smartphone, one controller, one processing system, and so on). As used herein, a device can include any electronic device with one or more parts that may implement at least some portions of this disclosure. While the description and examples use the term "device" to describe various aspects of this disclosure, the term "device" is not limited to a specific configuration, type, or number of objects. Additionally, the term "system" is not limited to multiple components or specific examples. For example, a system may be implemented on one or more printed circuit boards or other substrates, and may have movable or static components. While the description and examples use the term "system" to describe various aspects of this disclosure, the term "system" is not limited to a specific configuration, type, or number of objects.

Specific details are provided in the description to provide a thorough understanding of the aspects and examples provided herein. However, it will be understood by one of ordinary skill in the art that the aspects may be practiced without these specific details. For clarity of explanation, in some instances the present technology may be presented as including individual functional blocks including functional blocks comprising devices, device components, steps or routines in a method embodied in software, or combinations of hardware and software. Additional components may be used other than those shown in the figures and/or described herein. For example, circuits, systems, networks, processes, and other components may be shown as components in block diagram form in order not to obscure the aspects in unnecessary detail. In other instances, well-known circuits, processes, algorithms, structures, and techniques may be shown without unnecessary detail in order to avoid obscuring the examples.

Individual aspects and/or examples may be described above as a process or method which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

Processes and methods according to the above-described examples can be implemented using computer-executable instructions that are stored or otherwise available from computer-readable media. Such instructions can include, for example, instructions and data which cause or otherwise configure a general-purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as flash memory, memory or memory devices, magnetic or optical disks, flash memory, USB devices provided with non-volatile memory, networked storage devices, compact disk (CD) or digital versatile disk (DVD), any suitable combination thereof, among others. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

In some aspects, the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Devices implementing processes and methods according to these disclosures can include hardware, software, firmware, middleware, microcode, hardware description languages, or any combination thereof, and can take any of a variety of form factors. When implemented in software, firmware, middleware, or microcode, the program code or code segments to perform the necessary tasks (e.g., a computer-program product) may be stored in a computer-readable or machine-readable medium. A processor(s) may perform the necessary tasks. Typical examples of form factors include laptops, smart phones, mobile phones, tablet devices or other small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific examples thereof, but those skilled in the art will recognize that the application is not limited thereto. Thus, while illustrative examples of the application have been described in detail herein, it is to be understood that the inventive concepts may be otherwise variously embodied and employed, and that the appended claims are intended to be construed to include such variations, except as limited by the prior art. Various features and aspects of the above-described application may be used individually or jointly. Further, aspects of the present disclosure can be utilized in any number of environments and applications beyond those described herein without departing from the scope of the specification. The specification and drawings are, accordingly, to be regarded as illustrative rather than restrictive. For the purposes of illustration, methods were described in a particular order. It should be appreciated that in alternate examples, the methods may be performed in a different order than that described.

One of ordinary skill will appreciate that the less than ("<") and greater than (">") symbols or terminology used herein can be replaced with less than or equal to ("≤") and greater than or equal to ("≥") symbols, respectively, without departing from the scope of this description.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The phrase "coupled to" refers to any component that is physically connected to another component either directly or indirectly, and/or any component that is in communication with another component (e.g., connected to the other component over a wired or wireless connection, and/or other suitable communication interface) either directly or indirectly.

Claim language or other language reciting "at least one of" a set and/or "one or more" of a set indicates that one member of the set or multiple members of the set (in any combination) satisfy the claim. For example, claim language reciting "at least one of A and B" or "at least one of A or B" means A, B, or A and B. In another example, claim language reciting "at least one of A, B, and C" or "at least one of A, B, or C" means A, B, C, or A and B, or A and C, or B and C, or A and B and C. The language "at least one of" a set and/or "one or more" of a set does not limit the set to the items listed in the set. For example, claim language reciting "at least one of A and B" or "at least one of A or B" can mean A, B, or A and B, and can additionally include items not listed in the set of A and B.

The various illustrative logical blocks, modules, circuits, and algorithm steps described in connection with the examples disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random-access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein.

What is claimed is:

1. An apparatus for processing text data, the apparatus comprising:
at least one memory; and
at least one processor coupled to the at least one memory, the at least one processor configured to:
obtain an input text data, the input text data indicative of one or more pathologies associated with a corresponding radiological image, wherein the one or more pathologies are included in a plurality of pathologies;
generate, using a Bidirectional Encoder Representations from Transformers (BERT)-based machine learning network, a plurality of location tags associated with the input text data, wherein each respective location tag of the plurality of location tags is associated with a sentence included in the input text data and is indicative of an anatomical location;
generate a plurality of sentence groups based on the input text data and the plurality of location tags, wherein each sentence group of the plurality of sentence groups includes one or more sentences that are included in the input text data and are associated with a respective location tag indicative of a same respective anatomical location; and
generate, using a multi-task learning (MTL)-based machine learning network, a plurality of sets of features, wherein each set of features of the plurality of sets of features:
is generated based on a particular sentence group of the plurality of sentence groups; and
is indicative of a plurality of pathology severity predictions determined for the respective anatomical location associated with the particular sentence group.

2. The apparatus of claim 1, wherein the BERT-based machine learning network includes:
a plurality of BERT output layers; and
one or more Adapter machine learning networks, wherein each Adapter machine learning network is provided between a pair of BERT output layers included in the plurality of BERT output layers.

3. The apparatus of claim 2, wherein each BERT output layer of the plurality of BERT output layers is associated with at least one Adapter machine learning network.

4. The apparatus of claim 2, wherein the same one or more Adapter machine learning networks are utilized to generate the plurality of pathology severity predictions for each pathology of the plurality of pathologies.

5. The apparatus of claim 2, wherein:
the plurality of BERT output layers are associated with a first set of learned weights; and
each Adapter machine learning network comprises a multi-layer feedforward network associated with a second set of learned weights, wherein the second set of learned weights are trained based on freezing the first set of learned weights associated with the plurality of BERT output layers.

6. The apparatus of claim 1, wherein the plurality of sets of features includes a pathology severity prediction for each pathology of the plurality of pathologies at each respective anatomical location.

7. The apparatus of claim 1, wherein each set of features:
is associated with a different sentence group of the plurality of sentence groups;

is associated with a different respective anatomical location of a plurality of anatomical locations in the corresponding radiological image.

8. The apparatus of claim 6, wherein each set of features of the plurality of sets of features is generated using a respective classifier head included in the MTL-based machine learning network.

9. The apparatus of claim 1, wherein the MTL-based machine learning network comprises a second BERT-based machine learning network.

10. The apparatus of claim 1, wherein each respective location tag is associated with a sentence included in the input text data and is indicative of an anatomical location in the corresponding radiological image.

11. The apparatus of claim 10, wherein the corresponding radiological image is a cervical spine radiological image and each respective location tag is indicative of a particular motion segment of the cervical spine.

12. The apparatus of claim 1, wherein the MTL-based machine learning network includes a plurality of jointly trained classifier heads, each jointly trained classifier head of the plurality of jointly trained classifier heads associated with a particular pathology of the plurality of pathologies.

13. The apparatus of claim 12, wherein the plurality of pathology severity predictions determined for each respective anatomical location are generated based on:
   analyzing the particular sentence group associated with each respective anatomical location using the plurality of jointly trained classifier heads; and
   determining, for each respective anatomical location, a pathology severity prediction for each pathology of the plurality of pathologies, wherein each jointly trained classifier head of the plurality of jointly trained classifier heads generates a pathology severity prediction associated with a different pathology.

14. The apparatus of claim 12, wherein:
   each jointly trained classifier head is used to generate a respective sub-set of features associated with the particular pathology of the plurality of pathologies.

15. The apparatus of claim 1, wherein the input text data comprises a radiological report text indicative of one or more clinical findings associated with the corresponding radiological image.

16. A method for processing text data, comprising:
   obtaining an input text data indicative of one or more pathologies associated with a corresponding radiological image, wherein the one or more pathologies are included in a plurality of pathologies;
   generating, using a Bidirectional Encoder Representations from Transformers (BERT)-based machine learning network, a plurality of location tags associated with the input text data, wherein each respective location tag of the plurality of location tags is associated with a sentence included in the input text data and is indicative of an anatomical location of a plurality of anatomical locations in the corresponding radiological image;
   generating a plurality of sentence groups based on the input text data and the plurality of location tags, wherein each sentence group of the plurality of sentence groups includes one or more sentences that are included in the input text data and are associated with a respective location tag indicative of a same respective anatomical location; and
   generating, using a multi-task learning (MTL)-based machine learning network, a plurality of sets of features, wherein each set of features of the plurality of sets of features:
      is generated based on a particular sentence group of the plurality of sentence groups; and
      is indicative of a plurality of pathology severity predictions determined for the respective anatomical location associated with the particular sentence group.

17. The method of claim 16, wherein the BERT-based machine learning network includes:
   a plurality of BERT output layers; and
   one or more Adapter machine learning networks, wherein each Adapter machine learning network is provided between a pair of BERT output layers included in the plurality of BERT output layers.

18. The method of claim 16, wherein:
   the plurality of sets of features includes a pathology severity prediction for each pathology of the plurality of pathologies at each respective anatomical location; and
   each set of features of the plurality of sets of features is associated with a different sentence group of the plurality of sentence group and a different anatomical location of a plurality of anatomical locations in the corresponding radiological image;
   each respective location tag is associated with a sentence included in the input text data and is indicative of an anatomical location in the corresponding radiological image.

19. The method of claim 16, wherein the MTL-based machine learning network includes a plurality of jointly trained classifier heads, each jointly trained classifier head of the plurality of jointly trained classifier heads associated with a particular pathology of the plurality of pathologies.

20. The method of claim 19, wherein the plurality of pathology severity predictions determined for each respective anatomical location are generated based on:
   analyzing the particular sentence group associated with each respective anatomical location using the plurality of jointly trained classifier heads; and
   determining, for each respective anatomical location, a pathology severity prediction for each pathology of the plurality of pathologies, wherein each jointly trained classifier head of the plurality of jointly trained classifier heads generates a pathology severity prediction associated with a different pathology.

* * * * *